(12) United States Patent
Okada et al.

(10) Patent No.: US 11,234,962 B2
(45) Date of Patent: Feb. 1, 2022

(54) PHARMACEUTICAL COMPOSITION AND METHOD OF MANUFACTURING THE SAME

(71) Applicant: FUJIFILM Toyama Chemical Co., Ltd., Tokyo (JP)

(72) Inventors: Kotaro Okada, Ashigarakami-gun (JP); Yoshinori Sakata, Ashigarakami-gun (JP); Shigetomo Tsujihata, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/474,393

(22) PCT Filed: Dec. 28, 2017

(86) PCT No.: PCT/JP2017/047252
§ 371 (c)(1),
(2) Date: Jun. 27, 2019

(87) PCT Pub. No.: WO2018/124282
PCT Pub. Date: Jul. 5, 2018

(65) Prior Publication Data
US 2019/0343795 A1  Nov. 14, 2019

(30) Foreign Application Priority Data
Dec. 28, 2016  (JP) .............................. JP2016-255623

(51) Int. Cl.
*A61K 31/397*  (2006.01)
*A61K 9/00*  (2006.01)
(Continued)

(52) U.S. Cl.
CPC .......... *A61K 31/397* (2013.01); *A61K 9/0053* (2013.01); *A61K 9/0056* (2013.01);
(Continued)

(58) Field of Classification Search
None
See application file for complete search history.

(56) References Cited

U.S. PATENT DOCUMENTS

2005/0070521 A1  3/2005  Saitoh et al.
2010/0184997 A1  7/2010  Fukushima et al.
(Continued)

FOREIGN PATENT DOCUMENTS

CN  101501026 A  8/2009
CN  104159583 A  11/2014
(Continued)

OTHER PUBLICATIONS

Machine-assisted English translation for WO 2015/119289 A1 (Sakata et al). (Year: 2015).*
(Continued)

*Primary Examiner* — Sin J Lee
(74) *Attorney, Agent, or Firm* — Sughrue Mion, PLLC (57) ABSTRACT

An object of the present invention is to provide a pharmaceutical composition comprising 1-(3-(2-(1-benzothiophen-5-yl)ethoxy)propyl)azetidin-3-ol or a salt thereof at a high concentration, with a characteristic bitter taste masked, and a manufacturing method thereof. The present invention provides a pharmaceutical composition comprising fine granules having a core comprising 1-(3-(2-(1-benzothiophen-5-yl)ethoxy)propyl)azetidin-3-ol or a salt thereof, and a binder; and a polymer layer with which a surface of the core is coated, wherein the fine granules have a roundness of 0.8 or more and a content of 1-(3-(2-(1-benzothiophen-5-yl)ethoxy)propyl)azetidin-3-ol or the salt thereof in the fine granules is 30 to 90% by mass.

4 Claims, 1 Drawing Sheet

(51) Int. Cl.
    *A61K 9/16*         (2006.01)
    *A61K 9/20*         (2006.01)
    *A61P 25/00*       (2006.01)
    *A61P 43/00*       (2006.01)

(52) U.S. Cl.
    CPC .............. *A61K 9/16* (2013.01); *A61K 9/1635* (2013.01); *A61K 9/1652* (2013.01); *A61K 9/20* (2013.01); *A61K 9/2027* (2013.01); *A61K 9/2054* (2013.01); *A61P 25/00* (2018.01); *A61P 43/00* (2018.01)

(56) References Cited

U.S. PATENT DOCUMENTS

| | | |
|---|---|---|
| 2015/0045345 A1 | 2/2015 | Inaba et al. |
| 2016/0045446 A1* | 2/2016 | Shibata ................ A61K 9/1635 424/465 |
| 2016/0089338 A1 | 3/2016 | Kawano et al. |
| 2017/0165227 A1 | 6/2017 | Takahashi et al. |

FOREIGN PATENT DOCUMENTS

| | | | |
|---|---|---|---|
| EP | 2 818 165 A1 | 12/2014 | |
| JP | H06-116140 A | 4/1994 | |
| JP | 2009-256344 A | 11/2009 | |
| JP | 2013-237651 A | 11/2013 | |
| JP | 2015-98470 A | 5/2015 | |
| JP | 2015-129124 A | 7/2015 | |
| JP | 2016-6025 A | 1/2016 | |
| JP | 2016-141630 A | 8/2016 | |
| WO | 03/035647 A1 | 5/2003 | |
| WO | 2008/016107 A1 | 2/2008 | |
| WO | 2013/125617 A1 | 8/2013 | |
| WO | 2014/189034 A1 | 11/2014 | |
| WO | 2015/115582 A1 | 8/2015 | |
| WO | 2015/119289 A1 | 8/2015 | |

OTHER PUBLICATIONS

Machine-assisted English translation for JP 2013-237651 (Katayama et al). (Year: 2013).*
JPO English abstract for JP 2013-237651 (Katayama et al). (Year: 2013).*
Machine-assisted English translation for the claims of WO 2015/119289 A1 (Sakata et al). (Year: 2015).*
"Manufacturing of granules for tableting using a polygonal roller press and tableting properties, Mie Prefectural Science and Technology Promotion Center and others", 4 pages total.
International Search Report dated Mar. 13, 2018, issued by the International Searching Authority in corresponding application No. PCT/JP2017/047252.
Written Opinion dated Mar. 13, 2018, issued by the International Searching Authority in corresponding application No. PCT/JP2017/047252.
International Preliminary Report on Patentability dated Jul. 2, 2019, issued by the International Bureau in corresponding application No. PCT/JP2017/047252.
"Manufacturing of granules for tableting using a polygonal roller press and tableting properties, Mie Prefectural Science and Technology Promotion Center and others", presented at the 2003 Standard Meeting of the Society of Powder Technology, Japan, 4 pages total, 2003.
Extended European Search Report dated Nov. 27, 2019, from the European Patent Office in counterpart European Application No. 17885924.5.
Office Action dated Oct. 11, 2021 from the China National Intellectual Property Administration in Chinese Application No. 201780081229.4
Office Action dated Nov. 9, 2021 from the Japanese Patent Office in Japanese Application No. 2018-559634.

* cited by examiner

PHARMACEUTICAL COMPOSITION AND METHOD OF MANUFACTURING THE SAME

CROSS REFERENCE TO RELATED APPLICATIONS

This application is a National Stage of International Application No. PCT/JP2017/047252 filed Dec. 28, 2017, claiming priority based on Japanese Patent Application No. 2016-255623 filed Dec. 28, 2016.

TECHNICAL FIELD

The present invention relates to a pharmaceutical composition comprising fine granules having a core containing a predetermined drug, and a polymer layer, and a method of manufacturing the pharmaceutical composition.

BACKGROUND ART 1-(3-(2-(1-benzothiophen-5-yl)ethoxy)propyl)azetidin-3-ol (hereinafter also referred to as compound A) or a salt thereof has a neuroprotective action, a nerve regeneration promoting action, and a neurite outgrowth promoting action, and is a compound useful as a therapeutic agent for diseases of central and peripheral nerves (Patent Document 1).

Compound A or a salt thereof is orally administered, and as a pharmaceutical composition for oral administration, a solid pharmaceutical composition containing compound A or a salt thereof and one or two or more selected from mannitol, sorbitol, and isomaltose is known (Patent Document 2). Patients requiring compound A are mainly elderly people, and an easier-to-take formulation is desired.

Dry granulated powder containing no particles is known (Non-Patent Document 1). In addition, in Patent Document 2, granulation is performed using compound A by a dry granulation method of granulating without using core particles.

Meanwhile, Patent Document 3 discloses a multiple-unit type orally disintegrating tablet, which comprises enteric-coated fine granules containing acetylsalicylic acid, enteric-coated fine granules containing a proton pump inhibitor, and an additive, wherein an enteric coating layer of the enteric-coated fine granules containing acetylsalicylic acid comprises an aqueous enteric polymer base and a sustained-release base.

Patent Document 4 discloses a sustained-release granule, wherein two or more granules that are coated with a water-insoluble coating, having different average particle sizes and a particle size distribution in the range of 250 μm or less, are mixed.

PRIOR ART DOCUMENTS

Patent Documents

Patent Document 1: International Publication No. WO 2003/035647
Patent Document 2: International Publication No. WO 2013/125617
Patent Document 3: International Publication No. WO 2014/189034
Patent Document 4: JP Patent Publication (Kokai) No. 6-116140A (1994)

Non-Patent Document 1: Manufacturing of granules for tableting using a polygonal roller press and tableting properties, Mie Prefectural Science and Technology Promotion Center and others

SUMMARY OF INVENTION

Object to be Solved by the Invention

Orally disintegrating tablets and granules are known as easy-to-take formulations, and problems are that compound A has a characteristic bitterness and that a larger dosage thereof worsens the ease of taking (swallowability).

Dry granulated powder not comprising core particles disclosed in Non-Patent Document 1 has a large particle size distribution and thus, is unsuitable for coating. The technique disclosed in Patent Document 3 has the following drawback: since a drug substance or a polymer is used to coat a core particle thereby to increase an amount of additives, the ease of taking (swallowability) is worsened when the technique is applied to a drug that requires a large dosage. A problem of the sustained-release granule disclosed in Patent Document 4 is that use of a large amount of a coating agent worsens the ease of taking and further delays dissolution in the digestive tract. As described above, it has been desired to provide an easy-to-take pharmaceutical composition, which comprises a high concentration of compound A having a characteristic bitterness, with the characteristic bitter taste of compound A masked.

An object of the present invention is to provide a pharmaceutical composition comprising compound A or a salt thereof at a high concentration, with a characteristic bitter taste of compound A or the salt thereof masked, and a manufacturing method thereof. Further, another object of the present invention is to provide a pharmaceutical composition exhibiting good dissolution properties in the digestive tract while masking bitter taste in the oral cavity, and a manufacturing method thereof.

Means for Solving the Object

The present inventors have intensively studied to solve the above problems, and found that a pharmaceutical composition, which has solved the above problems, can be provided by manufacturing of a fine granule by way of: forming a core comprising compound A or a salt thereof and a binder; and then, coating a surface of the core with a polymer layer. Thus, they have completed the present invention.

Specifically, the present invention provides the following.
(1) A pharmaceutical composition comprising fine granules having a core comprising 1-(3-(2-(1-benzothiophen-5-yl)ethoxy)propyl)azetidin-3-ol or a salt thereof, and a binder, and a polymer layer with which a surface of the core is coated, wherein the fine granules have a roundness of 0.8 or more and a content of 1-(3-(2-(1-benzothiophen-5-yl)ethoxy)propyl)azetidin-3-ol or the salt thereof in the fine granules is 30 to 90% by mass.
(2) The pharmaceutical composition according to (1), wherein the content of 1-(3-(2-(1-benzothiophen-5-yl)ethoxy)propyl)azetidin-3-ol or the salt thereof in the fine granules is 50 to 90% by mass.
(3) The pharmaceutical composition according to (1) or (2), wherein the binder is one or more selected from the group consisting of hydroxypropyl cellulose, hydroxypropyl methyl cellulose, methyl cellulose, carmellose sodium, gum arabic, pregelatinized starch, polyvinyl alcohol, and polyvinyl alcohol/polyethylene glycol graft polymer.

(4) The pharmaceutical composition according to (1) or (2), wherein the binder is hydroxypropyl cellulose.

(5) The pharmaceutical composition according to any one of (1) to (4), wherein the polymer layer comprises at least one selected from the group consisting of ammonioalkyl methacrylate copolymer, methacrylic acid copolymer, ethyl cellulose, and ethyl acrylate/methyl methacrylate copolymer.

(6) The pharmaceutical composition according to any one of (1) to (5), further comprising an overcoat layer with which a surface of the polymer layer is coated.

(7) The pharmaceutical composition according to any one of (1) to (6), wherein the composition is a fine granule or a tablet.

(8) The pharmaceutical composition according to any one of (1) to (6), wherein the composition is an orally disintegrating tablet.

(9) A method of manufacturing the pharmaceutical composition according to any one of (1) to (8), the method comprising: a step of manufacturing a core comprising 1-(3-(2-(1-benzothiophen-5-yl)ethoxy)propyl)azetidin-3-ol or a salt thereof, and a binder by a wet agitation granulation method using 1-(3-(2-(1-benzothiophen-5-yl)ethoxy)propyl)azetidin-3-ol or the salt thereof and the binder; and a step of forming a polymer layer on a surface of the core.

Advantageous Effects of Invention

The present invention provides an easy-to-take pharmaceutical composition, which comprises compound A at a high concentration, with a characteristic bitter taste of compound A masked.

EMBODIMENT OF CARRYING OUT THE INVENTION

In the present description, the numerical range shown using "to" means a range which includes the numerical value described before and after "to" as the minimum value and the maximum value, respectively.

In the present description, the amount of each component in the composition is, when a plurality of substances corresponding to the component are present in the composition, the total amount of the plurality of substances present in the composition, unless otherwise stated.

In the present description, "average particle size" means volume average particle size (Mv), which is a value measured using a laser diffraction scattering type particle size distribution measuring apparatus (product name: LS 13 320, Beckman Coulter, Inc.), and the method of measuring the average particle size is not particularly limited.

In the present description, the term "layer" includes not only the configuration of coating the entirety of the object to be coated and but also the configuration of coating a portion of the object to be coated.

Figure 1:
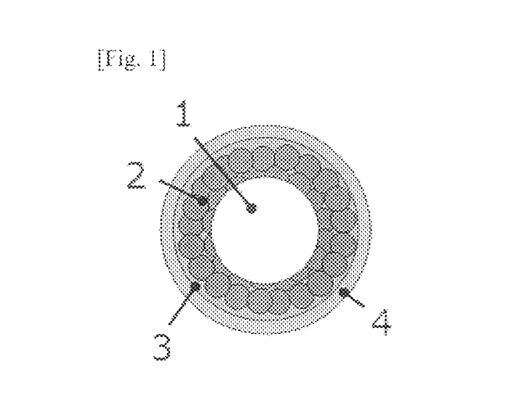
FIG. 1 shows a schematic view of a fine granule of the prior art.

A schematic view of a fine granule of the prior art is shown in FIG. 1. In the fine granule shown in FIG. 1, a surface of a core particle 1 is coated with an intermediate layer 3 containing a drug substance 2; and further, a surface of the intermediate layer is coated with a bitter taste masking layer 4. The fine granule shown in FIG. 1 enables a uniform coating of the intermediate layer 3 containing the drug substance 2, but does not allow an increased amount of the drug substance to be contained in one fine granule. It has been unsuitable for administration of over 400 mg of drug substance.

Figure 2:
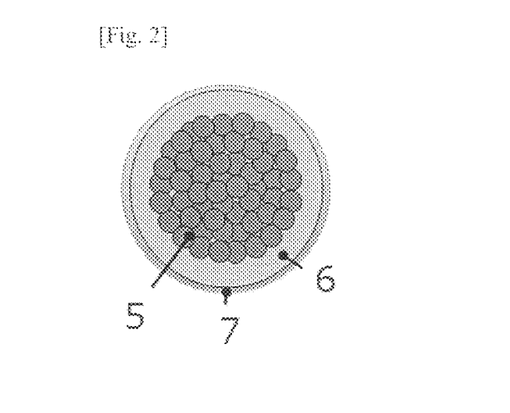
FIG. 2 shows a schematic view of an example of the fine granules of the present invention.

The schematic diagram of an example of the fine granules of the present invention is shown in FIG. 2. In the fine granules shown in FIG. 2, the surface of a core 5 containing the drug substance which is compound A is coated with a polymer layer 6, and the surface of the polymer layer 6 is further coated with an overcoat layer 7. The polymer layer 6 is a layer that functions as a bitter taste masking layer. The fine granules shown in FIG. 2 can increase the content of the drug substance contained in one granule.

In the present invention, it has been clarified that the fine granule is designed to have a sphericity of 0.8 or more, and this enhances a masking effect on the characteristic bitterness of compound A. Further, it has been found that a larger content of compound A or the salt thereof not only improves the ease of taking (swallowability) but also enhances the dissolution properties, which is an unexpected effect. In addition, for realizing the above fine granule, manufacturing of a core particle composed of a drug substance and a binder is necessary. It has been understood that use of a polymer such as hydroxypropyl cellulose (HPC) as a binder for wet agitation granulation allows manufacturing of a globular particle without damaging the stability of compound A.

[Pharmaceutical Composition]
(Fine Granule)

The pharmaceutical composition of the present invention comprises: fine granules having a core comprising compound A or a salt thereof, and a binder, and a polymer layer with which a surface of the core is coated, wherein the fine granules have a roundness of 0.8 or more and the content of compound A or the salt thereof in the fine granules is 30 to 90% by mass.

The core contains at least compound A or a salt thereof and the binder. The core preferably consists of core particles containing compound A or a salt thereof and the binder, and preferably does not contain core particles that do not contain compound A or a salt thereof. The method of preparing the core is not particularly limited, and a wet agitation method or the like is preferable. The method of preparing the core will be described below.

The surface of the core is coated with a polymer layer. The method of coating with a polymer layer is not specifically limited, and a method of spray-coating a core with the coating solution containing the polymer is preferable. The method of forming the polymer layer will be described below.

The roundness of the fine granules is 0.8 or more, preferably 0.82 or more, more preferably 0.83 or more, further more preferably 0.84 or more, still more preferably 0.86 or more, and particularly preferably 0.87 or more. The upper limit of the roundness of fine granules is not particularly limited, and is at most 1.0.

The roundness is determined by microscopic observation of 5 to 15 particles and calculation of $4\pi \times (area)/(square\ of\ perimeter)$ for the core using software (ImageJ, National Institutes of Health), and is expressed by the average value. In the case of a perfect circle, the roundness is 1.0.

<Compound A>

In the present invention, compound A (that is, 1-(3-(2-(1-benzothiophen-5-yl)ethoxy)propyl)azetidin-3-ol)) or a salt thereof is used as an active ingredient.

Since compound A has a cyclic amino group, examples of the salt thereof can include salts at commonly known basic groups.

Examples of salts at basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid, and salts with sulfonic acids such as methanesulfonic acid, benzenesulfonic acid, p-toluenesulfonic acid, mesitylene sulfonic acid, and naphthalene sulfonic acid.

Among the above salts, preferable salts are pharmacologically acceptable salts and more preferable salts are salts with maleic acid.

In the case of having isomers (for example, optical isomers, geometric isomers, and tautomers), compound A or a salt thereof may be any of all these isomers and may be any of hydrates, solvates, and all crystal forms.

Compound A or a salt thereof can be manufactured by methods known per se or an appropriate combination thereof, or a method disclosed in Patent Document 1.

The content of compound A or a salt thereof in the fine granules is 30 to 90% by mass, preferably 40 to 90% by mass, more preferably 50 to 90% by mass, still more preferably 55 to 90% by mass, and particularly preferably 55 to 80% by mass.

<Binder>

In the present invention, the binder to be used can be mixed with compound A or a salt thereof to form the core. The type of a substance is not particularly limited. Examples of the binder include hydroxypropyl cellulose, hydroxypropyl methyl cellulose, methyl cellulose, carmellose sodium, gum arabic, pregelatinized starch, polyvinyl alcohol (PVA), and polyvinyl alcohol/polyethylene glycol graft polymer. The binders may be used singly or in combinations of two or more. Among them, the binder is preferably hydroxypropyl cellulose, gum arabic, pregelatinized starch, or PVA, and particularly preferably hydroxypropyl cellulose.

The amount of a binder used is not particularly limited, and is preferably 2 to 30% by mass, more preferably 3 to 30% by mass, further more preferably 3 to 20% by mass, still more preferably 5 to 20% by mass, and particularly preferably 5 to 15% by mass, based on the mass of compound A or the salt thereof.

<Additive in Core>

The core may consist of compound A or a salt thereof and the binder, or may be added with additives such as excipients, in addition to compound A or a salt thereof and the binder. Examples of additives may include sugars selected from crystalline cellulose, lactose monohydrate, sucrose, and glucose; sugar alcohol selected from mannitol, sorbitol, erythritol, maltitol, trehalose, xylitol, and isomalt; cellulose derivatives such as ethylcellulose, carmellose, carmellose calcium, croscarmellose sodium, and low substituted hydroxypropyl cellulose; starch derivatives such as sodium carboxymethyl starch and pregelatinized starch; polypyrrolidone derivatives such as crospovidone; cyclodextrins such as α-cyclodextrin, β-cyclodextrin, γ-cyclodextrin, hydroxypropyl β-cyclodextrin, and sulfobutylether β-cyclodextrin sodium; starches such as corn starch, potato starch, and partially pregelatinized starch; phosphates such as calcium hydrogen phosphate and anhydrous calcium hydrogen phosphate; and carbonates such as precipitated calcium carbonate, and lactose monohydrate is particularly preferable.

The content of additives such as excipients in the core is not particularly limited, and is generally 10 to 100% by mass based on the mass of compound A or the salt thereof.

<Polymer Layer>

In the present invention, a surface of the core is coated with a polymer layer. The type of a polymer constituting the polymer layer is not particularly limited as long as it can be used in the pharmaceutical composition, that is, pharmaceutically acceptable, and for example, ammonio alkyl methacrylate copolymer (such as product name: Eudragit® RS 100, which is a pH-independent sustained release coating), methacrylic acid copolymer, ethyl cellulose, and ethyl acrylate/methyl methacrylate copolymer (product name: Eudragit® NE30D, which is a pH-independent sustained release coating) can be used. As the polymer, one may be used alone, or two or more polymers may be used in combination. As the polymer, ethyl cellulose that enables the dissolution properties and the bitter taste masking to be compatible with each other is most preferable.

The amount of the polymer used is not particularly limited, and is preferably 5 to 100% by mass, more preferably 10 to 90% by mass, still more preferably 20 to 80% by mass, and particularly preferably 20 to 50% by mass based on the mass of compound A or the salt thereof.

The polymer layer may consist of the above described polymer or may comprise additives other than the above described polymer.

Examples of additives in the polymer layer include plasticizer (for example, triacetin and triethyl citrate), and surfactant (glyceryl monostearate, polysorbate 80 and the like), and are not particularly limited.

The amount of the above additive used is not particularly limited, and the content of each additive is generally 2 to 30% by mass based on the mass of the polymer.

<Overcoat Layer>

The fine granules may further have an overcoat layer with which the surface of the polymer layer is coated. The fine granules having the overcoat layer can further suppress adhesion or aggregation among fine granules.

The type of a component constituting the overcoat layer is not particularly limited as long as it can be used in the pharmaceutical composition, that is, pharmaceutically acceptable, and for example, excipients such as mannitol, anhydrous silicic acid (light anhydrous silicic acid and the like) can be used.

The content of the overcoat layer is generally 0.5% by mass to 20% by mass based on the total mass of the core, the polymer layer, and the overcoat layer.

<Average Particle Size of Fine Granules>

The average particle size of fine granules in the present invention is, for example, preferably 100 μm to 1000 μm, more preferably 100 μm to 750 μm, and still more preferably 100 μm to 500 μm. By setting the average particle size of the fine granules within the above range, the roughness in the oral cavity can be further reduced when the pharmaceutical composition is disintegrated in the oral cavity, and thus an unpleasant feeling of taking can be avoided.

[Method of Manufacturing Pharmaceutical Composition]

The pharmaceutical composition of the present invention can be manufactured by the manufacturing method comprising: a step of manufacturing the core comprising compound A or a salt thereof and the binder by the wet agitation granulation method using compound A or a salt thereof and the binder; and a step of forming the polymer layer on the surface of the above core.

<Manufacturing of Core Comprising Compound A or Salt Thereof and Binder>

The core can be manufactured by the wet agitation granulation method using compound A or a salt thereof and the binder. The wet agitation granulation method is a method of manufacturing aggregated particles of powder by agitating while adding a suitable liquid binder to a fine powder.

The wet agitation granulation method can be performed using an agitated granulator. An example of an agitated granulator can include vertical granulator model FM-VG-01, manufactured by Powrex Corporation, and is not particularly limited.

The aqueous solution of the binder can be sprayed while agitating compound A or a salt thereof and the binder in the agitated granulator. Then, the agitation is further performed, and a granulated material can be obtained.

The agitation speed at spraying the aqueous solution of the binder is not particularly limited, and the blade rotational speed can be preferably 200 rpm to 400 rpm and more preferably 250 rpm to 300 rpm, and the cross screw rotational speed can be preferably 1000 rpm to 4000 rpm and more preferably 2000 rpm to 3000 rpm.

The agitation speed of the agitation after spraying the aqueous solution of the binder is not particularly limited, and the blade rotational speed can be preferably 600 rpm to 1000 rpm and more preferably 700 rpm to 900 rpm, and the cross screw rotational speed can be preferably 1000 rpm to 4000 rpm and more preferably 2000 rpm to 3000 rpm.

Drying the granulated material obtained above allows manufacturing of a core comprising compound A or a salt thereof and a binder. Drying can be performed using a fluidized bed granulator (for example, model FD-MP-01, manufactured by Powrex Corporation).

<Step of Forming Polymer Layer on Surface of Core>

The step of forming the polymer layer on the surface of the core can be performed by a general coating method. For example, a coating solution for a polymer layer may be prepared by dissolving the components constituting the polymer layer in a solvent and sprayed onto the core. The spray speed, spray time, solution temperature, drying conditions, and the like of the coating solution for a polymer layer are not particularly limited, and may be appropriately set according to the composition of the coating solution for a polymer layer, viscosity, particle size, and the like.

<Step of Forming Overcoat Layer on Surface of Polymer Layer>

Forming the overcoat layer on the surface of the polymer layer can manufacture fine granules having the overcoat layer with which the surface of the polymer layer is coated. However, the overcoat layer may or may not be provided.

The step of forming the overcoat layer can be performed by a general coating method and a powder addition method. For example, a coating solution for an overcoat layer may be prepared by dissolving the components constituting the overcoat layer in a solvent and sprayed onto the surface of the polymer layer. The spray speed, spray time, solution temperature, drying conditions, and the like of the coating solution for an overcoat layer are not particularly limited, and may be appropriately set according to the composition of the coating solution for an overcoat layer, viscosity, particle size, and the like. In the powder addition method, the components constituting the overcoat layer may be added in the form of a powder and mixed.

[Form of Pharmaceutical Composition]

The form of the pharmaceutical composition of the present invention is not particularly limited, and is preferably a solid formulation for oral use such as fine granules, tablets, and granules, and more preferably fine granules or tablets. The tablet is preferably an orally disintegrating tablet.

The tablet can be conventional coated tablets, for example, sugar-coated tablets, gelatin-encapsulated tablets, gastric-coated tablets, enteric-coated tablets, and water-soluble film-coated tablets, as required.

The tablet may be preferably an orally disintegrating tablet.

The orally disintegrating tablet may further comprise an excipient component outside the fine granules. The excipient component as used herein is a component that can contribute to improvement in the formability and the ease of taking of the tablet comprising fine granules. The excipient component may comprise pharmacologically acceptable pharmaceutical additives such as bitter taste inhibitors, odor adsorbents, excipients, disintegrants, lubricants, binders, fluidizers, sweeteners, flavors, and coloring agents, in the range which does not inhibit the effect of the present invention. The pharmaceutical additive may be one in which one component performs two or more functions. Specific examples of the excipient component can include those described in paragraph Nos. 0085 to 0095 of JP Patent Publication (Kokai) No. 2016-141630.

As the pharmaceutical additive, one may be used alone, or two or more may be used in combination.

The content of pharmaceutical additives in the excipient component comprised outside of fine granules can be set appropriately in consideration of the content ratio of fine granules in the orally disintegrating tablet, the average particle size of the fine granules, and the like.

[Properties of Pharmaceutical Composition]

When the pharmaceutical composition of the present invention is a tablet, 40 to 1000 mg of compound A or a salt thereof per tablet is preferably comprised.

The shape of the pharmaceutical composition of the present invention is not particularly limited as long as it is pharmaceutically acceptable.

When the pharmaceutical composition of the present invention is a tablet, the shape of the tablet may be, for example, a round tablet or a modified tablet, and can be appropriately set in consideration of drug compliance.

When the pharmaceutical composition of the present invention is a tablet, the size of the tablet is not particularly limited as long as it is pharmaceutically acceptable. From the view point that tablets are often used for patients who have difficulty swallowing, the size of the tablet of the present invention is preferably as small as possible in consideration of its medicinal effects.

In the pharmaceutical composition of the present invention, from the viewpoint of drug efficacy, dissolution rate after 60 minutes in the Japanese Pharmacopoeia dissolution test (paddle method: paddle rotation speed of 50 rpm, dissolution test solution: 0.1 mol/L hydrochloric acid) assuming dissolution of drug in the stomach is preferably 40% or more, more preferably 45% or more, further more preferably 50% or more, still more preferably 60% or more, yet still more preferably 70% or more, and particularly preferably 80% or more.

[Method of Manufacturing Tablets]

When the pharmaceutical composition of the present invention is a tablet, the method of manufacturing the tablet is not particularly limited, and known methods can be used. The tablet of the present invention can be obtained, for example, by mixing fine granules and, if desired, an excipient component, tableting the obtained mixed powder, and drying it.

The method of mixing the fine granules and the excipient component is not particularly limited. Examples of the method of mixing the fine granules and the excipient component include a method of mixing using a known mixer such as a V-type mixer (Tsutsui Scientific Instruments Co., Ltd.) and a fluidized bed granulator (Powrex Corporation).

The conditions such as the time required for mixing can be appropriately adjusted depending on the types of fine granules and the excipient component.

The method of tableting the mixed powder of fine granules and an excipient component is not particularly limited. The temperature at tableting is not particularly limited, and can be appropriately set.

An example of the method of tableting the mixed powder of fine granules and an excipient component includes a method of tableting using a tableting machine such as a rotary tableting machine (product name: HT-AP-SS, Hata Tekkosho Co., Ltd.) or a high-speed rotary type tableting machine (product name: AQUARIUS G, Kikusui Seisakusho Ltd.).

Method of drying tableted material obtained by tableting the mixed powder is not particularly limited. Examples of the method of drying tableted material obtained by tableting the mixed powder include a method of drying by vacuum drying, fluidized bed drying, or the like.

[Administration of Pharmaceutical Composition]

The administration method, dosage, and frequency of administration of the pharmaceutical composition of the present invention can be appropriately selected according to the age, body weight, and symptoms of the patient. The dose that can exert its medicinal effects may be typically administrated in a single dose or in several divided doses a day, and the dose of compound A or a salt thereof, for example, 40 to 1000 mg may typically be administrated to an adult in a single dose or in several divided doses a day.

Hereinafter, the present invention will be described in detail by the following Examples, but the present invention is not limited to these Examples.

The unit of a numerical value of each component in Table 1 to Table 5 and Table 7 described below is in parts by mass.

EXAMPLES

Example 1 (Wet Agitation)

(Formation of Core)

268.8 g of the maleate of compound A and 25.2 g of hydroxypropyl cellulose (HPC-L: product name, Nippon Soda Co., Ltd.) were placed in an agitation granulator (vertical granulator model FM-VG-01, manufactured by Powrex Corporation) and sprayed with 60.0 g of 10% by mass of hydroxypropyl cellulose (HPC-L: product name, Nippon Soda Co., Ltd.) aqueous solution while agitated at a blade rotation speed of 270 rpm and a cross screw rotation speed of 2500 rpm. Then, agitation was performed for 9 minutes at a blade rotation speed of 800 rpm and a cross screw rotation speed of 2500 rpm. The whole amount of the obtained granulated material was dried using a fluidized bed granulator (model FD-MP-01, manufactured by Powrex Corporation) at an air supply temperature of 60° C. to obtain a core.

(Formation of Polymer Layer)

Among the obtained cores, a core having a particle size of 100 μm to 355 μm was recovered using a sieve; 10 g of the core was placed in a micro fluidized-bed apparatus (manufactured by Dalton) which was a fluidized bed granulator; the air supply temperature was set to room temperature (30 to 40° C.); a coating solution containing an ammonioalkyl methacrylate copolymer dispersion (Eudragit RS30D: product name Evonik), triethyl citrate (Citroflex 2: product name, Morimura Bros., Inc.), glyceryl monostearate (Riken Vitamin Co., Ltd.), Polysorbate 80 (NOF Corporation) and purified water was fed into the micro fluidized-bed apparatus at a rate of 0.2 to 0.3 g/minute to perform spray coating; and thereby a polymer layer was formed.

(Formation of Overcoat Layer)

After forming the polymer layer, a coating solution containing light anhydrous silicic acid and purified water (the content of light anhydrous silicic acid is 14%) was fed into the micro fluidized-bed apparatus at a rate of 0.3 g/minute to obtain particles comprising an overcoat layer on the surface of the polymer layer. Among the obtained particles, particles having a particle size of 100 μm to 425 μm were recovered using a sieve and used for various evaluations.

Examples 2 to 5 (Wet Agitation) and Comparative Example 1 (Wet Agitation)

(Formation of Core)

A core was obtained in the same manner as in Example 1 except that the amount of hydroxypropyl cellulose was changed to the respective amount described in Table 1 and Table 2 and lactose monohydrate was used in Examples 4 and 5 in such a way as to provide the amount described in Table 1.

(Formation of Polymer Layer)

A polymer layer was formed in the same manner as in Example 1 except that the composition of the coating solution was changed to the respective composition shown in Table 1 and Table 2.

(Formation of Overcoat Layer)

A particle comprising an overcoat layer on a surface of the polymer layer was obtained in the same manner as in Example 1 except that the composition of the coating solution was changed to the respective composition shown in Table 1 and Table 2. Among the obtained particles, particles having a particle size of 100 μm to 425 μm were recovered using a sieve and used for various evaluations.

Comparative Example 2 (Wurster)

(Formation of Core)

400 g of D-mannitol (particle) (product name: Nonpareil-108, particle size range: 150 μm to 250 μm, Freund Corporation) as core particles was fed to a fluidized bed granulator (model: MP-01 (SPC), Powrex Corporation); the air supply temperature and the air supply rate to the fluidized bed granulator were adjusted to 60° C. and 0.5 m³/h to 1 m³/hour, respectively; a coating solution containing the maleate of compound A, hydroxypropyl cellulose (HPC-SSL: product name, Nippon Soda Co., Ltd.), talc (Crown Talc: product name, Matsumura Sangyo Co., Ltd.) and purified water was sprayed onto the core particles at a rate of about 2 g/min for coating; and thereby cores were obtained.

(Formation of Polymer Layer)

A polymer layer was formed in the same manner as in Example 1 except that the composition of the coating solution was changed to the composition shown in Table 2.

(Formation of Overcoat Layer)

A particle comprising an overcoat layer on a surface of the polymer layer was obtained in the same manner as in Example 1 except that the composition of the coating solution was changed to the composition shown in Table 2.

Among the obtained particles, particles having a particle size of 100 μm to 425 μm were recovered using a sieve and used for various evaluations.

Comparative Example 3 (Mortar)

(Formation of Core)

The maleate of compound A, D-mannitol (Mannit P: product name, Mitsubishi Shoji Foodtech Co., Ltd.), talc (Crown Talc: product name, Matsumura Sangyo Co., Ltd.), and hydroxypropyl cellulose (HPC-L: product name, Nippon Soda Co., Ltd.) were placed in a mortar, and Japanese Pharmacopoeia purified water was added thereinto while the mixture was stirred with a pestle. Thereafter, particle size selection was conducted with a 500 μm-sieve; drying was conducted by a shelf type dryer at 50° C. for 12 hours; and thereby cores were obtained.

(Formation of Polymer Layer)

A polymer layer was formed in the same manner as in Example 1 except that the composition of the coating solution was changed to the composition shown in Table 2.

(Formation of Overcoat Layer)

A particle comprising an overcoat layer on a surface of the polymer layer was obtained in the same manner as in Example 1 except that the composition of the coating solution was changed to the composition shown in Table 2. Among the obtained particles, particles having a particle size of 100 μm to 425 μm were recovered using a sieve and used for various evaluations.

Comparative Example 4 (Roller Compactor)

(Formation of Core)

D-mannitol, ethyl cellulose, crystalline cellulose, Crospovidone, croscarmellose sodium and magnesium stearate were added to and mixed with the maleate of compound A for 30 minutes. The mixed powder was compression molded using a dry granulator, and molded solids were subjected to particle size selection to obtain core particles.

(Formation of Polymer Layer)

A polymer layer was formed in the same manner as in Example 1.

(Formation of Overcoat Layer)

A particle comprising an overcoat layer on a surface of the polymer layer was obtained in the same manner as in Example 1. Among the obtained particles, particles having a particle size of 100 μm to 425 μm were recovered and used for various evaluations.

Comparative Example 5 (Roller Compactor)

(Formation of Core)

Magnesium stearate was added to and mixed with the maleate of compound A for 30 minutes. The mixed powder was compression molded by a dry granulator, and molded solids were subjected to particle size selection to obtain particles.

(Formation of Polymer Layer)

A polymer layer was formed in the same manner as in Example 1 except that the composition of the coating solution was changed to the composition shown in Table 2.

(Formation of Overcoat Layer)

A particle comprising an overcoat layer on a surface of the polymer layer was obtained in the same manner as in Example 1. Among the obtained particles, particles having a particle size of 100 μm to 425 μm were recovered using a sieve and used for various evaluations.

Examples 6 to 14 (Wet Agitation)

(Formation of Core)

A core was obtained in the same manner as in Example 1 except that the amount of each component was changed to the respective amount described in Table 3 to Table 5.

(Formation of Polymer Layer)

A polymer layer was formed in the same manner as in Example 1 except that the composition of the coating solution was changed to the respective composition shown in Table 3 to Table 5.

(Formation of Overcoat Layer)

A particle comprising an overcoat layer on a surface of the polymer layer was obtained in the same manner as in Example 1 except that the composition of the coating solution was changed to the respective composition shown in Table 3 to Table 5. Among the obtained particles, particles having a particle size of 100 μm to 425 μm were recovered using a sieve and used for various evaluations.

[Evaluation]

The following items were evaluated for the pharmaceutical compositions manufactured in Examples and Comparative Examples. The results of the evaluation are shown in Table 1 to Table 5.

<Roundness>

The roundness is determined by microscopic observation of 5 to 15 fine granules and calculation of $4\pi \times (\text{area})/(\text{square of perimeter})$ for the fine granules using software (ImageJ, National Institutes of Health), and is expressed by the average value.

<Evaluation of Bitter Taste>

The bitter taste of compound A or a salt thereof has not only a bitter taste felt when contained in the oral cavity (pre-bitter taste) and but also a bitter taste which persists after swallowing (post-bitter taste). That is, compound A or a salt thereof is a compound having both the pre-bitter taste and the post-bitter taste.

Evaluation was performed using a taste sensing system (Intelligent Sensor Technology, Inc.: SA402B). This taste sensing system is a device capable of taking out a change in the membrane potential of the artificial lipid membrane as a signal, and a relative value corresponding to the pre-taste can be obtained. The relative value is defined as follows:

Relative value: Vs–Vr

Vr (mV): Measured value of reference solution before measuring control solution or sample solution Vs (mV): Measured value of the control solution or sample solution The measurement was performed three times, and the average value was calculated for each relative value of the control solution and each sample solution.

In the taste sensing system, after stabilization with reference solutions (30 mM KCl and 0.3 mM tartaric acid), relative values in the control solution and each sample solution were measured. As the sensor used for measurement, AC0 specific to basic bitter taste was used.

Separately, a sensory test was performed, and a calibration curve was created from the correlation between the bitter taste score of the sensory and the relative value. The bitter taste score was calculated by interpolating the relative value from the calibration curve.

Bitter Taste Score of Sensory:
1 Bitter taste that can be perceived at last
2 Understandable bitter taste
3 Bitter taste that can be perceived easily
4 Strong bitter taste
5 Unbearable bitter taste The test method is as follows.

A sample was added to Japanese Pharmacopoeia purified water such that the concentration of the maleate of compound A was 9 mg/mL, and mixed by inversion for 30 seconds. The solution was immediately filtered through a polysilicate glass fiber, and the solution to which KCl was added such that the KCl concentration in the filtrate was 10 mmol/L was used as a sample solution. In addition, a 10 mmol/L KCl solution was used as a control solution.

<Evaluation of Pre-Bitter Taste>
A The score was 0 or more to less than 1.5
B The score was 1.5 or more to less than 2.5
C The score was 2.5 or more <Feeling of Taking (Swallowability)>
A case where the mass of the composition was less than 1.0 g was defined as A; a case for 1.0 g or more to less than 1.5 g was defined as B; and a case for 1.5 g or more was defined as C.

<Comprehensive Evaluation>
The evaluation criteria for the comprehensive evaluation are as follows:

A: A case that the evaluation of bitter taste is A and the evaluation of feeling of taking (swallowability) is A; or a case that the evaluation of bitter taste is B and the evaluation of feeling of taking (swallowability) is A B: A case that the evaluation of bitter taste is A and the evaluation of feeling of taking (swallowability) is B; or a case that the evaluation of bitter taste is B and the evaluation of feeling of taking (swallowability) is B C: A case that at least one of the evaluation of bitter taste and the evaluation of feeling of taking (swallowability) is C <Dissolution>
A dissolution test was performed in accordance with the dissolution test described in 16th revised Japanese Pharmacopoeia. The dissolution test was performed by a paddle method (paddle rotation speed: 50 rpm) using a dissolution test machine DT-810 of JASCO Corporation. As a dissolution test solution, 0.1 mol/L hydrochloric acid (volume: 900 mL) was used and degassed by a Media Prep of Nihon Validation Technologies Corporation; and then, the temperature therefor was maintained at 37±0.5° C.

The amounts of compound A released from a sample for a testing period of 60 minutes were measured using an ultraviolet spectrophotometer at wavelengths of 257 nm and 500 nm, and a dissolution rate (%) from a difference therebetween was calculated.

[Table 1]

TABLE 1

| | | Sphericity, content | | | | |
|---|---|---|---|---|---|---|
| | | Wet agitation Example 1 | Wet agitation Example 2 | Wet agitation Example 3 | Wet agitation Example 4 | Wet agitation Example 5 |
| Core | Maleate of compound A | 448 | 448 | 448 | 448 | 448 |
| | Hydroxypropyl cellulose | 52 | 37 | 52 | 69 | 69 |
| | Lactose monohydrate | | | | 379 | 379 |
| Polymer layer | Ethyl cellulose | | 157 | 56 | 326 | |
| | Triacetin | | 39 | 14 | 82 | |
| | Ammonioalkyl methacrylate copolymer | 203 | | | | |
| | Methacrylic acid copolymer LD | | | | | 349 |
| | Triethyl citrate | 10 | | | | 35 |
| | Glyceryl monostearate | 10 | | | | 17 |
| | Polysorbate 80 | 4 | | | | 7 |
| Overcoat layer | Mannitol | | 45 | | 80 | 94 |
| | Light anhydrous silicic acid | 7 | | 6 | | |
| | Content | 61% | 62% | 78% | 32% | 32% |
| | Roundness of fine granules | 0.87 | 0.87 | 0.83 | 0.86 | 0.84 |
| | Bitter taste | A | A | B | B | A |
| | Feeling of taking (swallowability) | A | A | A | B | B |
| | Comprehensive evaluation | A | A | A | B | B |

TABLE 2

| | | Sphericity, content | | | | |
|---|---|---|---|---|---|---|
| | | Wet agitation Comparative Example 1 | Wurster Comparative Example 2 | Mortar Comparative Example 3 | Roller Comparative Example 4 | Roller Comparative Example 5 |
| Core | Maleate of compound A | 448 | 448 | 448 | 448 | 448 |
| | Hydroxypropyl cellulose | 69 | 128 | 63 | | |
| | D-Mannitol | | 5,126 | 376 | 113 | |
| | Talc | | 64 | 9 | | |
| | Lactose monohydrate | 83 | | | | |
| | Ethyl cellulose | | | | 32 | |
| | Crystalline cellulose | | | | 13 | |

TABLE 2-continued

| | | Spherity, content | | | | |
|---|---|---|---|---|---|---|
| | | Wet agitation Comparative Example 1 | Wurster Comparative Example 2 | Mortar Comparative Example 3 | Roller Comparative Example 4 | Roller Comparative Example 5 |
| | Crospovidone | | | | 16 | |
| | Croscarmellose Na | | | | 3 | |
| | Mg stearate | | | | 6 | 3 |
| | L-aspartic acid | 296 | | | | |
| Polymer layer | Ethyl cellulose | | 698 | 153 | | 58 |
| | Triacetin | | | 38 | | 15 |
| | Ammonioalkyl methacrylate copolymer | 461 | | | 203 | |
| | Methacrylic acid copolymer LD | | | | | |
| | Triethyl citrate | 23 | 174 | | 10 | |
| | Glyceryl monostearate | 23 | | | 10 | |
| | Polysorbate 80 | 9 | | | 4 | |
| Overcoat layer | Mannitol | 111 | 563 | 62 | | |
| | Light anhydrous silicic acid | | | | 9 | 5 |
| | Content | 29% | 6% | 39% | 52% | 85% |
| | Roundness of fine granules | 0.86 | 0.89 | 0.79 | 0.79 | 0.78 |
| | Bitter taste | A | A | C | C | C |
| | Feeling of taking (swallowability) | C | C | B | A | A |
| | Comprehensive evaluation | C | C | C | C | C |

TABLE 3

| | | Example 6 | Example 7 | Example 8 | Example 9 |
|---|---|---|---|---|---|
| Core | Maleate of compound A | 448 | 448 | 448 | 448 |
| | Hydroxypropyl cellulose | 37 | 37 | 69 | 69 |
| | Lactose monohydrate | | | 379 | 379 |
| Polymer layer | Ethyl cellulose | 49 | 157 | 100 | 326 |
| | Triacetin | 12 | 39 | 25 | 82 |
| Overcoat layer | Mannitol | | 45 | | 80 |
| | Light anhydrous silicic acid | 5 | | 10 | |
| | Content of maleate of compound A | 81% | 62% | 43% | 32% |
| | Roundness | 0.87 | 0.87 | 0.82 | 0.86 |
| | Bitter taste | B | A | B | B |
| | Feeling of taking (swallowability) | A | A | B | B |
| | Dissolution | 86% | 88% | 77% | 75% |
| | Comprehensive evaluation | A | A | B | B |

TABLE 4

| | | Example 10 | Example 11 | Example 12 |
|---|---|---|---|---|
| Core | Maleate of compound A | 448 | 448 | 448 |
| | Hydroxypropyl cellulose | 69 | 52 | 25 |
| | Lactose monohydrate | 379 | | |
| Polymer layer | Ethyl cellulose | 100 | | 149 |
| | Ammonioalkyl methacrylate copolymer | | 203 | |
| | Ethyl acrylate/methyl methacrylate copolymer | | | 45 |
| | Triacetin | 25 | | 22 |
| | Triethyl citrate | | 10 | |
| | Glyceryl monostearate | | 10 | |
| | Polysorbate 80 | | 4 | |
| Overcoat layer | Mannitol | | | 84 |
| | Light anhydrous silicic acid | 10 | 7 | |
| | Content | 43% | 61% | 58% |
| | Roundness | 0.82 | 0.87 | 0.86 |
| | Bitter taste | B | A | A |
| | Dissolution | 77% | 93% | 92% |

TABLE 5

| | | Binder | |
|---|---|---|---|
| | | Example 13 | Example 14 |
| Core | Maleate of compound A | 448 | 448 |
| | Hydroxypropyl cellulose | 69 | |
| | Polyvinyl pyrrolidone | | 69 |
| | Lactose monohydrate | 379 | 379 |
| Polymer layer | Ethyl cellulose | 326 | 326 |
| | Triacetin | 82 | 82 |
| Overcoat layer | Mannitol | 80 | 80 |
| | Content | 32% | 32% |
| | Roundness | 0.86 | 0.84 |
| | Bitter taste | B | A |
| | Dissolution | 75% | 45% |

Reference Examples (Storage Stability)

Each component shown in Table 7 was mixed in such a way as to provide the composition shown in Table 7.

The obtained composition was subjected to a stress test that it was stored in a thermostat at 70° C. for 7 days and a test that it was stored for 1 month at 40° C. Then, the storage stability of the pharmaceutical composition was evaluated in terms of the amount of compound A decomposed by the following method.

The above stored pharmaceutical composition was dissolved in water/acetonitrile/pH 3.0 phosphate buffer (450:50:1) such that the maleate of compound A had 333 μg/mL and was filtered through a membrane filter to obtain a filtrate. The degradation material of compound A was quantified by high performance liquid chromatography (HPLC). The amount of the degradation material detected at a relative retention time of 0.94 with respect to compound A was quantified as the degradation material of compound A under the following measurement conditions. The amount of the degradation material (percentage relative to the amount of compound A) is shown in Table 7.

(HPLC Measurement Condition)
Detector: UV detector (detection wavelength: 230 nm)
Column: Waters Sunfire 3.0 mm×150 mm (3.5 μm)
Column temperature: 40° C.
Developing Solvent:
A; Water/acetonitrile/pH 3.0 phosphate buffer=38:7:5
B; Water/acetonitrile pH 3.0 phosphate buffer=11:7:2
Flow rate: 0.45 mL/min
Sample cooler temperature: 5° C.
Injection volume: 10 μL

TABLE 6

| Time (minute) | Concentration of developing solvent A (% by mass) | Concentration of developing solvent B (% by mass) |
| --- | --- | --- |
| 0 | 100 | 0 |
| 3 | 100 | 0 |
| 23 | 0 | 100 |
| 35 | 0 | 100 |
| 40 | 100 | 0 |
| 50 | 100 | 0 |

Examples 15 to 17

The fine granules in Example 12 and the excipient component were mixed in such a way as to provide the composition shown in Table 8, to obtain a tableted powder (mixed powder). The tableted powder (mixed powder) obtained was weighed out such that 448 mg of the maleate of compound A was contained in 3 tablets and was compression molded using a rotary tableting machine (product name: HT-AP-SS, Hata Tekkosho Co., Ltd.) with a 12 mmφ single R face punch at a rotational speed of 20 rpm in such a way as to provide a hardness of 50 N, to obtain an orally disintegrating tablet (tablet).

TABLE 8

|  | Example 15 | Example 16 | Example 17 |
| --- | --- | --- | --- |
| Fine granule of Example 12 | 50.0 | 49.3 | 49.3 |
| Granulated material of mannitol/corn starch | 18.1 | 17.8 | 17.8 |
| Crospovidone | 3.0 | 3.0 | 3.0 |
| Ethyl cellulose | 4.0 | 3.9 | 3.9 |
| Mg aluminometasilicate | 2.5 | 2.5 | 2.5 |
| Crystalline cellulose | 20.0 | 19.7 | 19.7 |
| Hydrous silicon dioxide | 1.0 | 1.0 | 1.0 |
| Aspartame | 1.0 | 1.0 | 1.0 |
| Strawberry micron | 0.1 | 0.1 | 0.1 |
| Ca stearate | 0.3 | 0.3 | 0.3 |
| Na Lauryl sulfate |  | 1.4 |  |
| L-aspartic acid |  |  | 1.4 |

[Evaluation of Orally Disintegrating Tablet]
<Evaluation of Bitter Taste Masking>
One orally disintegrating tablet was placed in the oral cavity of the subject. Evaluation was performed according to

TABLE 7

| Common name | Product name | Manufacturer | Reference Example 1 | Reference Example 2 | Reference Example 3 | Reference Example 4 | Reference Example 5 | Reference Example 6 | Reference Example 7 | Reference Example 8 |
| --- | --- | --- | --- | --- | --- | --- | --- | --- | --- | --- |
| Maleate of compound A | T-817MA | — | 448.0 | 448.0 | 448.0 | 448.0 | 448.0 | 448.0 | 448.0 | 448.0 |
| D-Mannitol | Mannit P | Mitsubishi Shoji Foodtech Co., Ltd. | 421.1 | 421.1 | 421.1 | 421.1 | 421.1 | 421.1 | 421.1 | 421.1 |
| Hydroxypropyl cellulose | NISSO HPC L | Nippon Soda Co., Ltd. | 17.9 |  |  |  |  |  |  |  |
| HPMC | TC-5 (R) R | Shin-Etsu Chemical Co., Ltd. |  | 17.9 |  |  |  |  |  |  |
| Methyl cellulose | METOLOSE (R) SM-15 | Shin-Etsu Chemical Co., Ltd. |  |  | 17.9 |  |  |  |  |  |
| Carmellose Na | Sergen (R) PR-S | DKS Co., Ltd. |  |  |  | 17.9 |  |  |  |  |
| Gum arabic | Gum arabic | Wako Pure Chemical Industries, Ltd. |  |  |  |  | 17.9 |  |  |  |
| Pregelatinized starch | SWELSTAR (TM) WB-1 | Asahi Kasei Chemicals Corp. |  |  |  |  |  | 17.9 |  |  |
| PVA | GOHSENOL (TM) EG-05P | Nippon Synthetic Chemical Industry Co., Ltd. |  |  |  |  |  |  | 17.9 |  |
| PVA/PEG/ grafted copolymer | Kollicoat IR | BASF |  |  |  |  |  |  |  | 17.9 |
| Talc | Crown Talc Pharmacopeia PP | Matsumura Sangyo Co., Ltd. | 9.0 | 9.0 | 9.0 | 9.0 | 9.0 | 9.0 | 9.0 | 9.0 |
| Total amount |  |  | 896.0 | 896.0 | 896.0 | 896.0 | 896.0 | 896.0 | 896.0 | 896.0 |
| Stability | 70° C., 7 days |  | 0.02% | 0.10% | 0.11% | 0.04% | 0.01% | 0.02% | 0.03% | 0.06% |
|  | 40° C., 1 month |  | 0.00% | 0.01% | 0.01% | 0.01% | 0.00% | 0.00% | 0.00% | 0.01% | the following evaluation criteria whether bitter taste derived from compound A remained 60 minutes after the placement.

Evaluation Criteria:

B A bitter taste was slightly felt 60 minutes after the placement

A No bitter taste was felt 60 minutes after the placement

The orally disintegrating tablets obtained in Examples 15 to 17 were subjected to sensory evaluation of bitter taste masking. As a result, for the orally disintegrating tablet in Example 15, a slight bitter taste was felt, but for the orally disintegrating tablets in Examples 16 and 17, no bitter taste was felt, and the bitter taste derived from compound A was sufficiently masked.

<Oral Disintegration Time>

One orally disintegrating tablet was dosed in the oral cavity of one adult male, and the time until the core of the tablet was not felt was measured.

The oral disintegration times of the orally disintegrating tablets in Examples 15 to 17 were measured. As a result, the oral disintegration times of Examples 15, 16 and 17 were 26 seconds, 41 seconds and 25 seconds, respectively.

REFERENCE SIGNS LIST

1 Core particle
2 Drug substance
3 Intermediate layer
4 Bitter taste masking layer
5 Core
6 Polymer layer
7 Overcoat layer

The invention claimed is:

1. Fine granules having a core consisting of 1-(3-(2-(1-benzothiophen-5-yl)ethoxy)propyl)azetidin-3-ol or a salt thereof and a binder; and a polymer layer with which a surface of the core is coated, wherein:

the fine granules have a roundness of 0.8 or more;
the content of 1-(3-(2-(1-benzothiophen-5-yl)ethoxy)propyl)azetidin-3-ol or the salt thereof in the fine granules is 50 to 90% by mass;
the binder is hydroxypropyl cellulose;
the polymer layer comprises at least one selected from the group consisting of ethyl cellulose, ammonioalkyl methacrylate copolymer, and ethyl acrylate/methyl methacrylate copolymer;
the amount of the polymer is 20 to 50% by mass based on the mass of 1-(3-(2-(1-benzothiophen-5-yl)ethoxy)propyl)azetidin-3-ol or the salt thereof; and
the amount of the binder in the core is 5 to 15% by mass based on the mass of 1-(3-(2-(1-benzothiophen-5-yl)ethoxy)propyl)azetidin-3-ol or the salt thereof.

2. The fine granules according to claim 1, wherein the polymer layer further comprises methacrylic acid copolymer.

3. The fine granules according to claim 1, further comprising an overcoat layer with which a surface of the polymer layer is coated.

4. A method of manufacturing the fine granules according to claim 1, the method comprising: a step of manufacturing a core consisting of 1-(3-(2-(1-benzothiophen-5-yl)ethoxy)propyl)azetidin-3-ol or a salt thereof and a binder by a wet agitation granulation method using 1-(3-(2-(1-benzothiophen-5-yl)ethoxy)propyl)azetidin-3-ol or the salt thereof and hydroxypropyl cellulose as the binder; and a step of forming a polymer layer on a surface of the core, wherein the polymer layer comprises at least one selected from the group consisting of ethyl cellulose, ammonioalkyl methacrylate copolymer, and ethyl acrylate/methyl methacrylate copolymer.

* * * * *